(12) United States Patent
Howard

(10) Patent No.: US 10,569,081 B2
(45) Date of Patent: Feb. 25, 2020

(54) STACKED POTENTIAL ELECTROPORATION

(71) Applicant: Medtronic, Inc., Minneapolis, MN (US)

(72) Inventor: Brian T. Howard, Bloomington, MN (US)

(73) Assignee: Medtronic, Inc., Minneapolis, MN (US)

( * ) Notice: Subject to any disclaimer, the term of this patent is extended or adjusted under 35 U.S.C. 154(b) by 137 days.

(21) Appl. No.: 15/448,912

(22) Filed: Mar. 3, 2017

(65) Prior Publication Data

US 2018/0250508 A1    Sep. 6, 2018

(51) Int. Cl.
| | |
|---|---|
| *A61N 1/32* | (2006.01) |
| *A61B 5/0402* | (2006.01) |
| *A61B 5/00* | (2006.01) |
| *A61B 5/053* | (2006.01) |
| *A61B 18/12* | (2006.01) |
| *A61B 18/00* | (2006.01) |

(52) U.S. Cl.
CPC ............ *A61N 1/327* (2013.01); *A61B 5/0008* (2013.01); *A61B 5/0402* (2013.01); *A61B 5/053* (2013.01); *A61B 18/1206* (2013.01); *A61B 2018/00613* (2013.01)

(58) Field of Classification Search
None
See application file for complete search history.

(56) References Cited

U.S. PATENT DOCUMENTS

| | | | | |
|---|---|---|---|---|
| 6,029,090 A | * | 2/2000 | Herbst | ............... A61N 1/0412 607/66 |
| 6,714,816 B1 | * | 3/2004 | Heller | .................. A61N 1/325 604/20 |
| 2005/0170510 A1 | * | 8/2005 | Huang | .................. C12M 35/02 435/459 |

(Continued)

FOREIGN PATENT DOCUMENTS

| | | |
|---|---|---|
| WO | 2015/175944 A1 | 11/2015 |
| WO | 2015/192027 A1 | 12/2015 |

OTHER PUBLICATIONS

International Search Report and Written Opinion dated May 18, 2018, for corresponding International Application No. PCT/US2018/020156; International Filing Date: Feb. 28, 2018 consisting of 14-pages.

*Primary Examiner* — Erica S Lee

(74) *Attorney, Agent, or Firm* — Christopher & Weisberg, P.A.

(57) ABSTRACT

A method of delivering pulsed electrical energy to a target tissue region includes delivering a first therapeutic pulse, the delivering of the first therapeutic pulse includes delivering a first pulse for a first time period, the first pulse having a first voltage amplitude. A second pulse is delivered immediately after the first pulse for a second time period, the second pulse having a second voltage amplitude configured to electroporate the target tissue region, the second time period being less than the first time period. A third pulse is delivered without delay after the second pulse for a third time period, the third pulse having a third voltage amplitude being at least one from the group consisting of substantially the same as the first amplitude, larger than the first amplitude, and less than the first amplitude.

9 Claims, 6 Drawing Sheets

(56) References Cited

U.S. PATENT DOCUMENTS

2012/0220998 A1* 8/2012 Long ................ A61B 18/1206
606/41
2016/0166310 A1 6/2016 Stewart et al.
2017/0035499 A1 2/2017 Stewart et al.
2018/0071014 A1* 3/2018 Neal ................ A61B 18/1477

* cited by examiner

STACKED POTENTIAL ELECTROPORATION

CROSS-REFERENCE TO RELATED APPLICATION n/a

STATEMENT REGARDING FEDERALLY SPONSORED RESEARCH OR DEVELOPMENT n/a

TECHNICAL FIELD

This disclosure relates to a method and system for increasing the effectiveness of electroporation.

BACKGROUND

In electroporation using pulse field ablation waveforms, the pores created by the application of voltage are generally considered to be short lived and sustained by the applied potential field. When a high voltage "pulse" is applied, pores are created and close shortly after the pulse has finished. However, after that initial process, the cell membrane remains disturbed for some period of time and is more permeable for a longer time period. During this extended period of permeability, a smaller voltage potential may be used, usually with a longer time duration, to drive polarized components, such as ions or even DNA, through the cell membrane. For example, as shown in FIG. 1, in current electroporation waveforms, a large amplitude pulse is followed by a delayed period in which no pulse is delivered, following by a low amplitude pulse that has a longer duration than the high amplitude pulse to drive charged components, such as ions or DNA, across the cell membrane and thus aid in the transfer of materials for any given electroporative purpose. However, standard pulse cycles all include this recovery period between the high amplitude pulses which allows the cellular pores to close and begins to decrease the permeability/recovery of the cells. In another example similar configuration may be used with the lower voltage preceding the higher voltage pulse which in general may be employed to drive components to or away from the target cell membrane in advance of the larger voltage pulse to initiate the onset of cell permeability which is initiated after a short transition period during which no pulse is applied.

SUMMARY

Some embodiments advantageously provide a method delivering pulsed electrical energy to a target tissue region. In one embodiment, the method of delivering pulsed electrical energy to a target tissue region includes delivering a first therapeutic pulse, the delivering of the first therapeutic pulse includes delivering a first pulse for a first time period, the first pulse having a first voltage amplitude. A second pulse is delivered immediately after the first pulse for a second time period, the second pulse having a second voltage amplitude configured to electroporate the target tissue region, the second time period being less than the first time period. A third pulse is delivered without delay after the second pulse for a third time period, the third pulse having a third voltage amplitude being at least one from the group consisting of substantially the same as the first amplitude, larger than the first amplitude, and less than the first amplitude.

In another aspect of this embodiment, delivering the first therapeutic pulse includes not delivering energy during a fourth time period, the fourth time period following the delivery of the third pulse and delivering a fourth pulse for a fifth time period, the fourth pulse having a fourth amplitude having a polarity opposite the polarity of the first pulse.

In another aspect of this embodiment, delivering the first therapeutic pulse includes delivering a fifth pulse after the fifth time period for a sixth time period, the fifth pulse having fifth voltage amplitude having a polarity opposite of the second pulse.

In another aspect of this embodiment, the third voltage amplitude is less than the second voltage amplitude.

In another aspect of this embodiment, the method further includes delivering between 1-200 therapeutic pulses per pulse train.

In another aspect of this embodiment, the first voltage amplitude is in the range of 1V to 400V.

In another aspect of this embodiment, the first time period is in the range between 4 µs and 500 ms.

In another aspect of this embodiment, the third time period is greater than the first time period.

In another aspect of this embodiment, the third time period is the same as the first time period.

In another aspect of this embodiment, the third time period is less than the first time period.

In another aspect of this embodiment, the third pulse has the same polarity as the first pulse and a different polarity than the second pulse.

In another embodiment, the method includes delivering a first therapeutic pulse, the delivering of the first therapeutic pulse includes delivering a first pulse for a first time period, the first pulse having a first voltage amplitude in the range of 1V to 400V. A second pulse is delivered immediately after the first pulse for a second time period, the second pulse having a second voltage amplitude configured to electroporate the target tissue region, the second time period being less than the first time period. A third pulse is delivered immediately after the second pulse for a third time period greater than the second time period, the third pulse having a third voltage amplitude substantially the same as the first amplitude.

In another aspect of this embodiment, the third pulse has the same polarity as the first pulse and a different polarity than the second pulse.

In another aspect of this embodiment, delivering the first therapeutic pulse includes not delivering energy during a fourth time period, the fourth time period following the delivery of the third pulse and delivering a fourth pulse for a fifth time period, the fourth pulse having a fourth amplitude having a polarity opposite the polarity of the first pulse.

In another aspect of this embodiment, delivering the first therapeutic pulse includes delivering a sixth pulse after the fifth time period for a sixth time period, the sixth pulse having fifth voltage amplitude having a polarity opposite of the second pulse.

In another aspect of this embodiment, the second pulse has the opposite polarity as the first pulse.

In another aspect of this embodiment, the first time period is in the range between 4 µs and 500 ms.

In another aspect of this embodiment, the method includes delivering 1-500 therapeutic pulse per pulse train.

In another aspect of this embodiment, the method includes delivering 1-10 pulse trains In another aspect of this embodiment, a series of therapeutic pulses, of a single or multiple polarities, or in pairs constituting a biphasic therapeutic pulses may be delivered with a fifth time separation. This time separation may itself be equal to the timing between the pairs of a biphasic therapeutic pulse which may range from 0-10 s.

In another aspect of this embodiment, the method further includes delivering the first pulse train and the second pulse train consecutively.

In another aspect of this embodiment, the method includes the initial polarity of a therapeutic pulse of a biphasic therapeutic pulse pair that may be different from that of a preceding pulse in a train of therapeutic pulses.

In another aspect of this embodiment, the method includes modification to the absolute and/or relative voltage levels in the voltage components comprising a therapeutic pulse with successive applications within a train or individual applications.

In yet another embodiment, the method includes delivering a first pulse for a first time period in the range of 4 µs and 500 ms, the first pulse having a first voltage amplitude in the range of 1V to 400V. A second pulse having a second pulse amplitude for a second time period is delivered, the second pulse amplitude being greater than the first voltage amplitude but not configured to electroporate the target tissue region. A third pulse is delivered immediately after the second pulse for a third time period, the third pulse having a third voltage amplitude configured to electroporate the target tissue region, the third time period being less than the first time period. A fourth pulse is delivered immediately after the third pulse for a fourth time period greater than the third time period, the fourth pulse having a fourth voltage amplitude substantially the same as the first amplitude.

BRIEF DESCRIPTION OF THE DRAWINGS

A more complete understanding of embodiments described herein, and the attendant advantages and features thereof, will be more readily understood by reference to the following detailed description when considered in conjunction with the accompanying drawings wherein.

DETAILED DESCRIPTION

Figure 1:
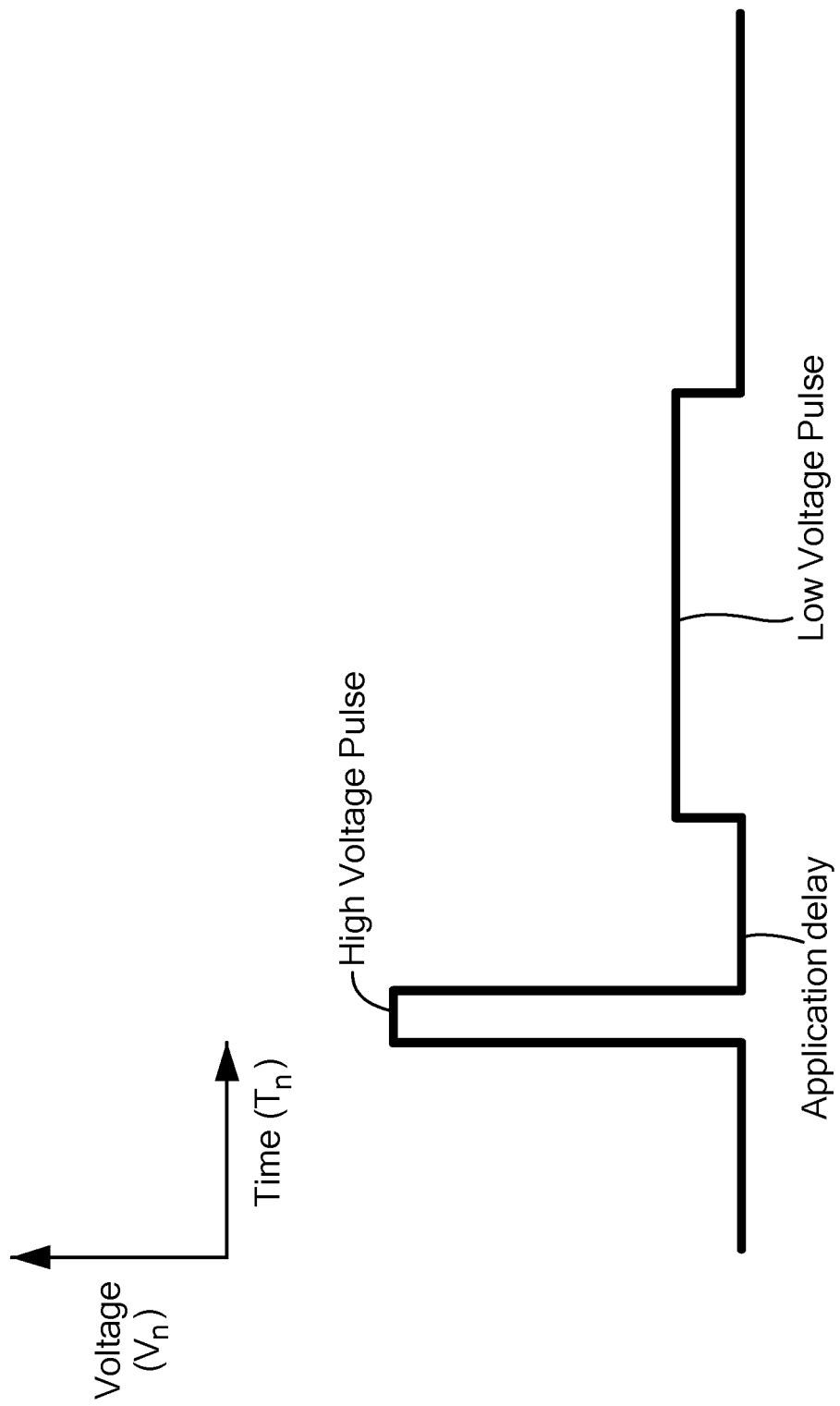
FIG. 1. is a diagram of a standard prior art electroporation pulse waveform.

Before describing in detail exemplary embodiments, it is noted that the embodiments reside primarily in combinations of apparatus components and processing steps related to stacked electroporation pulsed waveforms. Accordingly, the system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

By removing the delay between individual pulses of different amplitudes, a single therapeutic pulse is generated which lacks the intrinsic delay between the respective pulses which now comprise it, increasing the efficacy of the applied field. With an associated increase in efficacy, less energy, fewer pulses, or similar reductions in therapy may be required to achieve the desired results both in reversible and irreversible applications.

Figure 2:
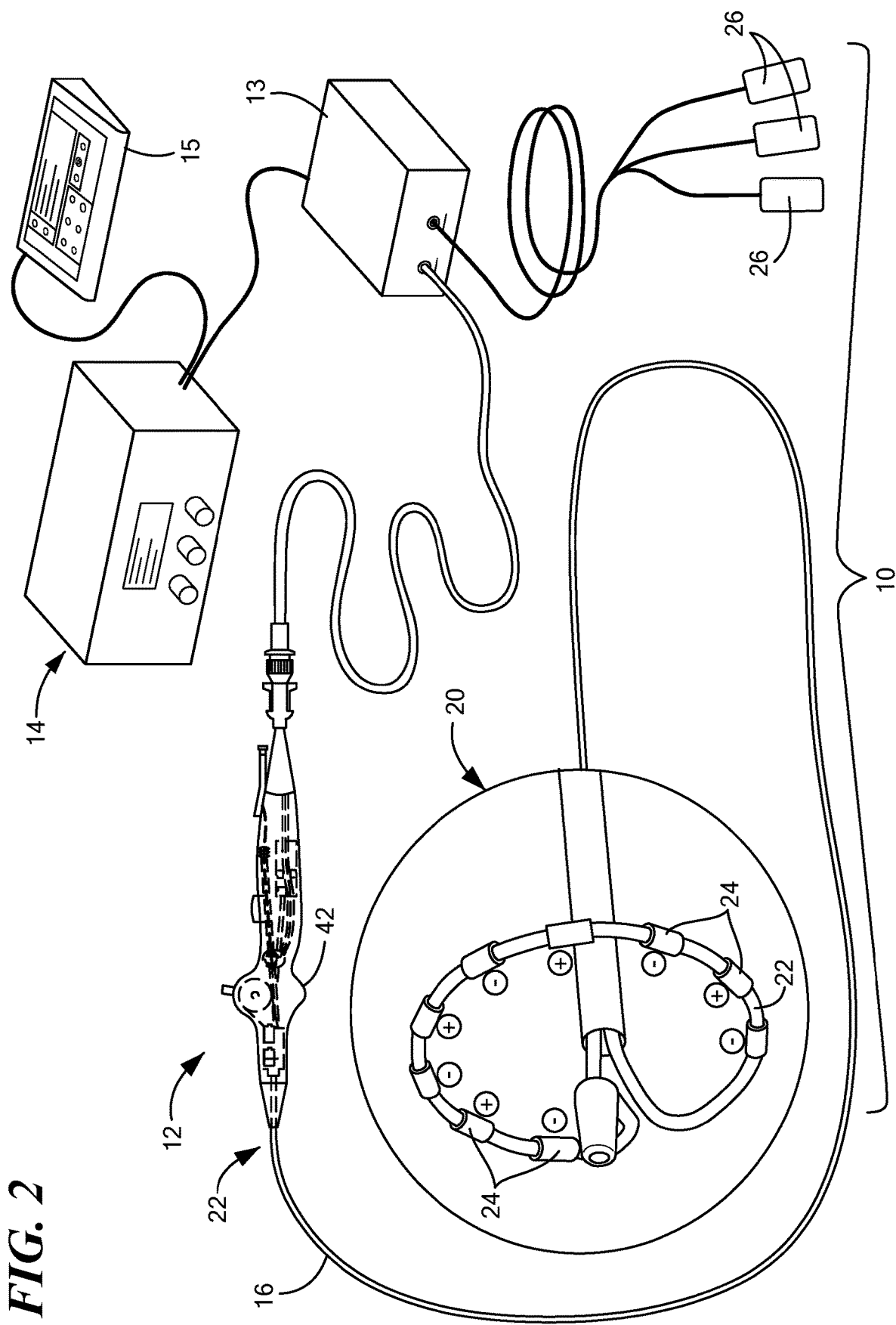
FIG. 2 is an exemplary electrosurgical generator with an associated hand piece for the delivery of PFA.

Referring now to the drawings where like reference designators refer to like elements there is shown in FIG. 2 an exemplary electrosurgical general configured to deliver electrical energy to irreversibly electroporate tissue and designated generally as "10." The system 10 generally includes a medical device 12 that may be coupled directly to an energy supply, for example, a pulse field ablation generator 14 including an energy control, delivering and monitoring system or indirectly through a catheter electrode distribution system 13. A remote controller 15 may further be included in communication with the generator for operating and controlling the various functions of the generator 14. The medical device 12 may generally include one or more diagnostic or treatment regions for energetic, therapeutic and/or investigatory interaction between the medical device 12 and a treatment site. The treatment region(s) may deliver, for example, pulsed electroporation energy to a tissue area in proximity to the treatment region(s).

The medical device 12 may include an elongate body 16 passable through a patient's vasculature and/or positionable proximate to a tissue region for diagnosis or treatment, such as a catheter, sheath, or intravascular introducer. The elongate body 16 may define a proximal portion 18 and a distal portion 20, and may further include one or more lumens disposed within the elongate body 16 thereby providing mechanical, electrical, and/or fluid communication between the proximal portion of the elongate body 16 and the distal portion of the elongate body 16. The distal portion 20 may generally define the one or more treatment region(s) of the medical device 12 hat are operable to monitor, diagnose, and/or treat a portion of a patient. The treatment region(s) may have a variety of configurations to facilitate such operation. In the case of purely bipolar pulsed field delivery, distal portion 20 includes electrodes that form the bipolar configuration for energy delivery. In an alternate configuration, a plurality of the electrodes 24 may serve as one pole while a second device containing one or more electrodes (not pictured) would be placed to serve as the opposing pole of the bipolar configuration. For example, as shown in FIG. 2, the distal portion 20 may include an electrode carrier arm 22 that is transitionable between a linear configuration and an expanded configuration in which the carrier arm 22 has an arcuate or substantially circular configuration. The carrier arm 22 may include the plurality of electrodes 24 (for example, nine electrodes 24, as shown in FIG. 2) that are configured to deliver pulsed-field energy. Further, the carrier arm 22 when in the expanded configuration may lie in a plane that is substantially orthogonal to the longitudinal axis of the elongate body 16. The planar orientation of the expanded carrier arm 22 may facilitate ease of placement of the plurality of electrodes 24 in contact with the target tissue. Alternatively, the medical device 12 may be have a linear configuration with the plurality of electrodes 24. For example, the distal portion 20 may include six electrodes 24 linearly disposed along a common longitudinal axis.

The generator 14 may include processing circuitry including a first processor 17 in communication with one or more controllers and/or memories containing software modules containing instructions or algorithms to provide for the automated operation and performance of the features, sequences, calculations, or procedures described herein. The system 10 may further include three or more surface ECG electrodes 26 on the patient in communication with the generator 14 through the catheter electrode distribution box 13 to monitor the patient's cardiac activity for use in determining pulse train delivery timing at the desired portion of the cardiac cycle, for example, during the ventricular refractory period. In addition to monitoring, recording or otherwise conveying measurements or conditions within the medical device 12 or the ambient environment at the distal portion of the medical device 12, additional measurements may be made through connections to the multi-electrode catheter including for example temperature, electrode-tissue interface impedance, delivered charge, current, power, voltage, work, or the like in the generator 14 and/or the medical device 12. The surface ECG electrodes 26 may be in communication with the generator 14 for initiating or triggering one or more alerts or therapeutic deliveries during operation of the medical device 12. Additional neutral electrode patient ground patches (not pictured) may be employed to evaluate the desired bipolar electrical path impedance, as well as monitor and alert the operator upon detection of inappropriate and/or unsafe conditions which include, for example, improper (either excessive or inadequate) delivery of charge, current, power, voltage and work performed by the plurality of electrodes 24; improper and/or excessive temperatures of the plurality of electrodes 24, improper electrode-tissue interface impedances; improper and/or inadvertent electrical connection to the patient prior to delivery of high voltage energy by delivering one or more low voltage test pulses to evaluate the integrity of the tissue electrical path.

The generator 14 may include an electrical current or pulse generator having a plurality of output channels, with each channel coupled to an individual electrode of the plurality of electrodes 24 or multiple electrodes of the plurality of electrodes 24 of the medical device 12. The generator 14 may be operable in one or more modes of operation, including for example: (i) bipolar energy delivery between at least two electrodes 24 or electrically-conductive portions of the medical device 12 within a patient's body, (ii) monopolar or unipolar energy delivery to one or more of the electrodes or electrically-conductive portions on the medical device 12 within a patient's body and through either a second device within the body (not shown) or a patient return or ground electrode (not shown) spaced apart from the plurality of electrodes 24 of the medical device 12, such as on a patient's skin or on an auxiliary device positioned within the patient away from the medical device 12, for example, and (iii) a combination of the monopolar and bipolar modes.

Figure 3:
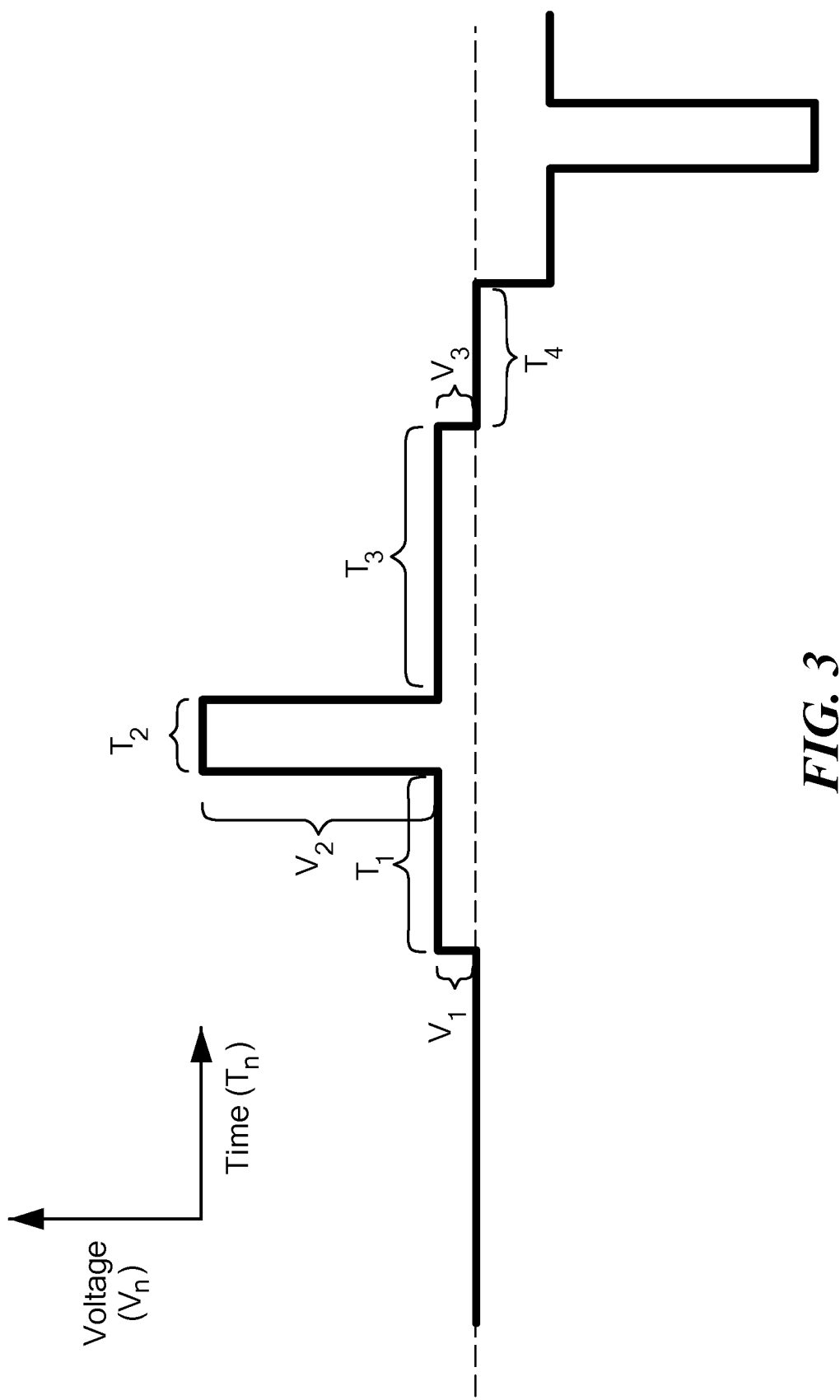
FIG. 3 is a diagram of a electroporation pulse waveform of the present application.

Referring now to FIG. 3, in which an exemplary voltage stacked electroporation pulsed waveform is shown for treatment of tissues within a human or animal patient, and in a particular configuration cardiac tissue or cancerous tissue. Instead of a large voltage pulse followed by an off-period following by a lower voltage pulse, the voltage potentials may be stacked together to reduce or eliminate the relaxation time between pulses that exists in current electroporation waveforms. For example, a first therapeutic pulse may include a preceding pulse V1 that is applied at the beginning of an exemplary stacked electroporation and may range in amplitude for 1V to 400V for a duration of T1, which may be for 4 μs to 500 ms. The function of V1 is to localize intracellular or extracellular components at or away from the cell membrane prior to permeabilization and/or increase the permeability of the target tissue and/or to increase the susceptibility of the target tissue to permeabilization by the following higher (in magnitude) voltage pulse. Because of the preceding pulse V1, a larger amplitude pulse V2 of the first therapeutic pulse, and its associated pulse width T2, which may be for 0.1 μs to 200 ms, may be reduced or increased in size from a standard electroporation pulse, whether to reversibly or irreversibly electroporate tissue, thus reducing the possibility of current leakage and increasing the safety of the procedure by reducing muscle stimulation or pain in procedure by increasing the effectiveness of a single application. For example, by removing the transition phase where no energy is delivered to the tissue between V1 and V2 the area of effect is increased for a similar large amplitude electroporating pulse, but conversely, a smaller amplitude voltage might be applied instead to affect the same region. Thus, by removing the transition phase between V1 and V2 keeps those charged components localized at (or away) from the membrane right until the membrane is permeabilized, reducing diffusion or concentration loss of those components.

Continuing to refer to FIG. 3, following the large amplitude pulse $V_2$ a trailing pulse $V_3$ of the first therapeutic pulse, which may be the same, less, than or greater than the amplitude of $V_1$, but less than $V_2$, and functions in a similar manner to $V_1$. The motive force applied by $V_3$ is not resisted as greatly by the newly permeabilized surface and further may assist in maintaining the permeabilization. The trailing pulse may also have a duration $T_3$ that is the same, less than, or greater than $T_1$, but greater than $T_2$. Similar to removing the time delay between $V_1$ and $V_2$, removing the time delay between $V_2$ and $V_3$ may deprive the cell membrane a recovery phase before these effects, such as applying the motive force to charged components to drive them across the membrane, are applied. In exemplary configuration, $T_1<=T_3$ and $V_1=V_3$. Following $V_3$, the stacked waveform may include an interphase period $T_4$ during which the voltage may be stepped down to the same or similar voltage to that before the application of $V_1$ to end that particular pulse. In one configuration, if biphasic pulses are applied, the polarity of $V_1$-$V_3$ and $T_1$-$T_4$ may be reversed after $T_4$ to complete one therapeutic pulse. The pattern of opposing polarities may be repeated for, for example, 1-500 therapeutic pulses per pulse train, and for 1-10 pulse trains.

Figure 4:
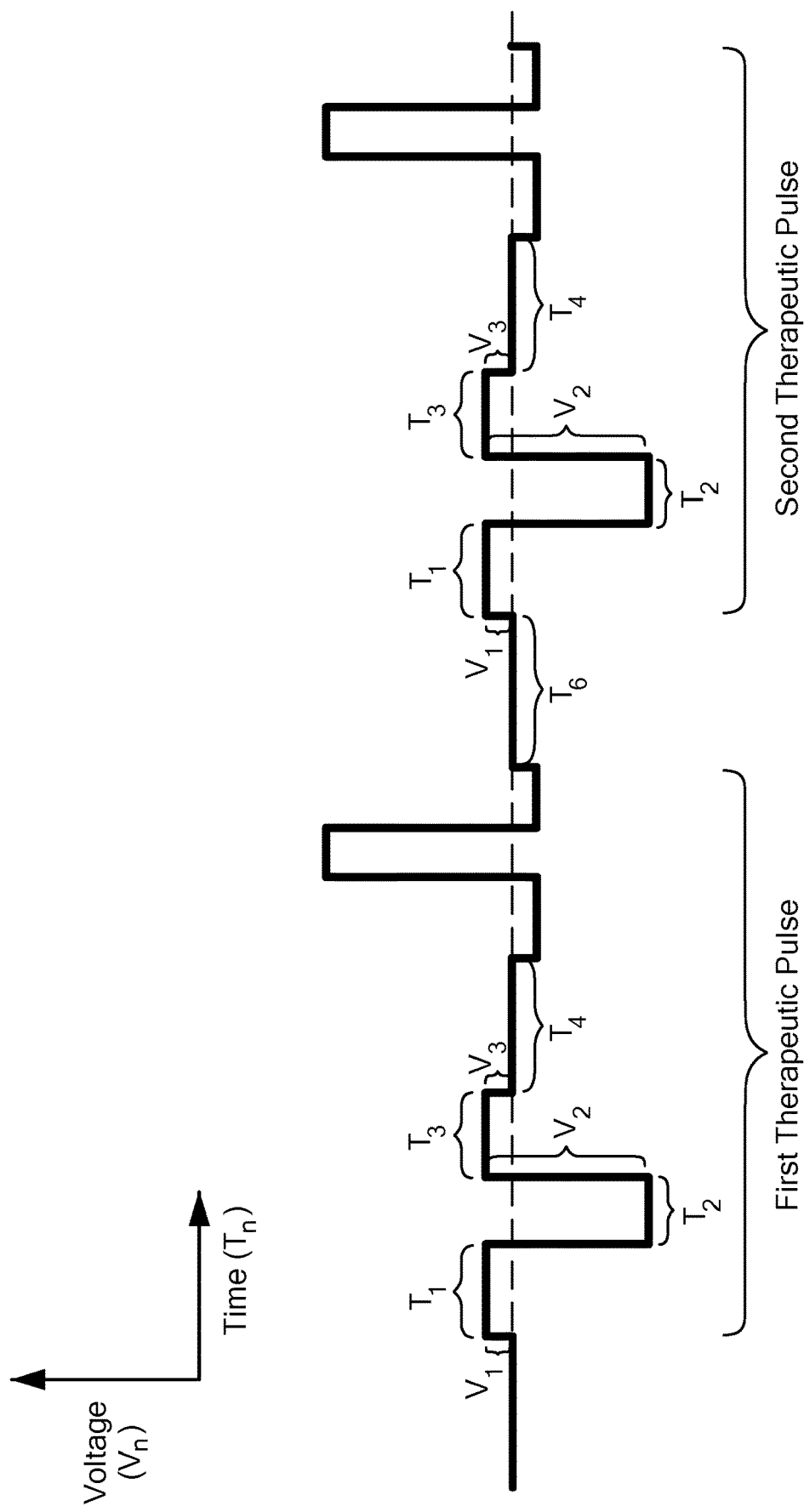
FIG. 4 is a diagram of another electroporation pulse waveform of the present application.
Figure 5:
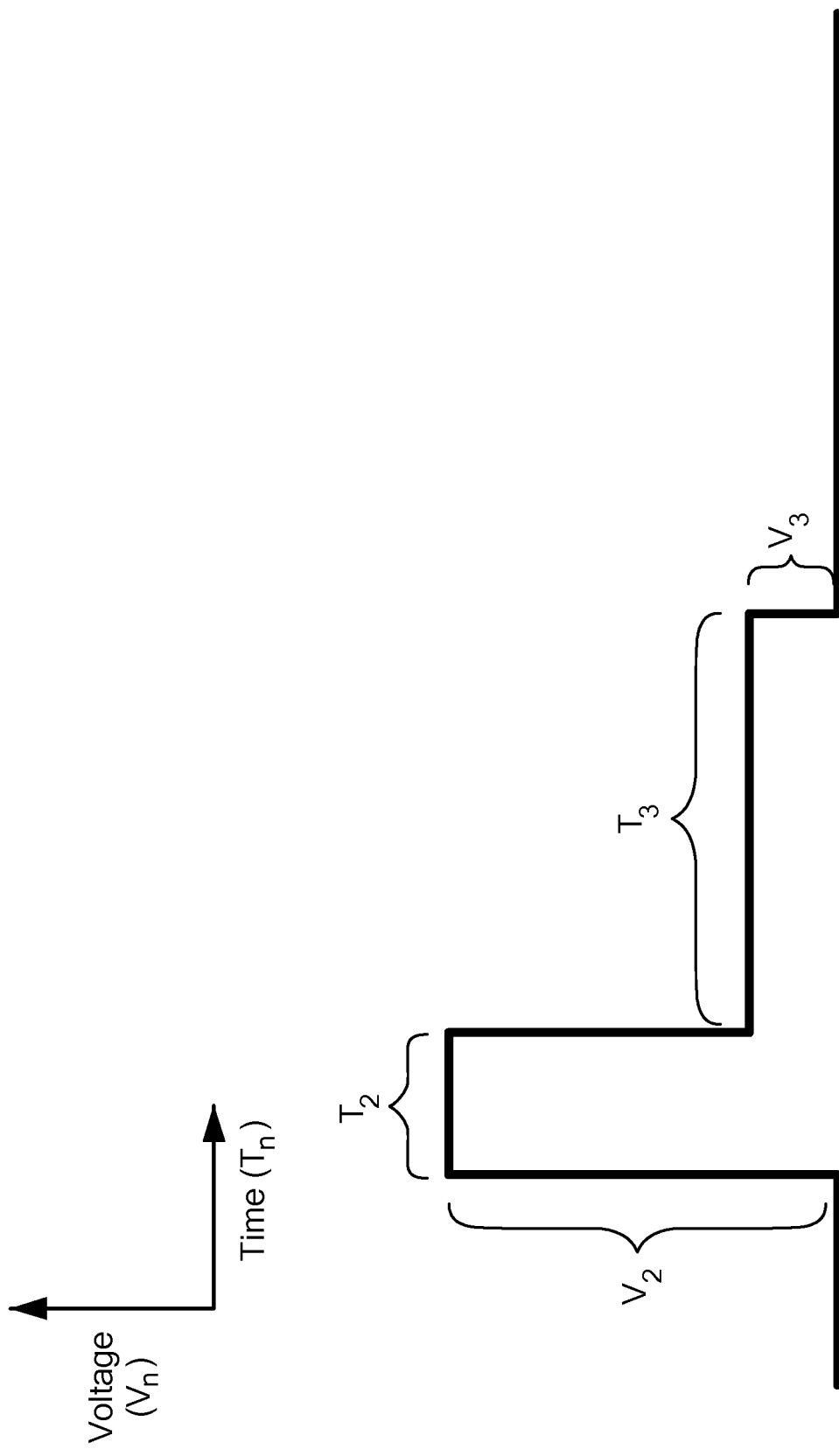
FIG. 5 is a diagram of another electroporation pulse waveform of the present application.
Figure 6:
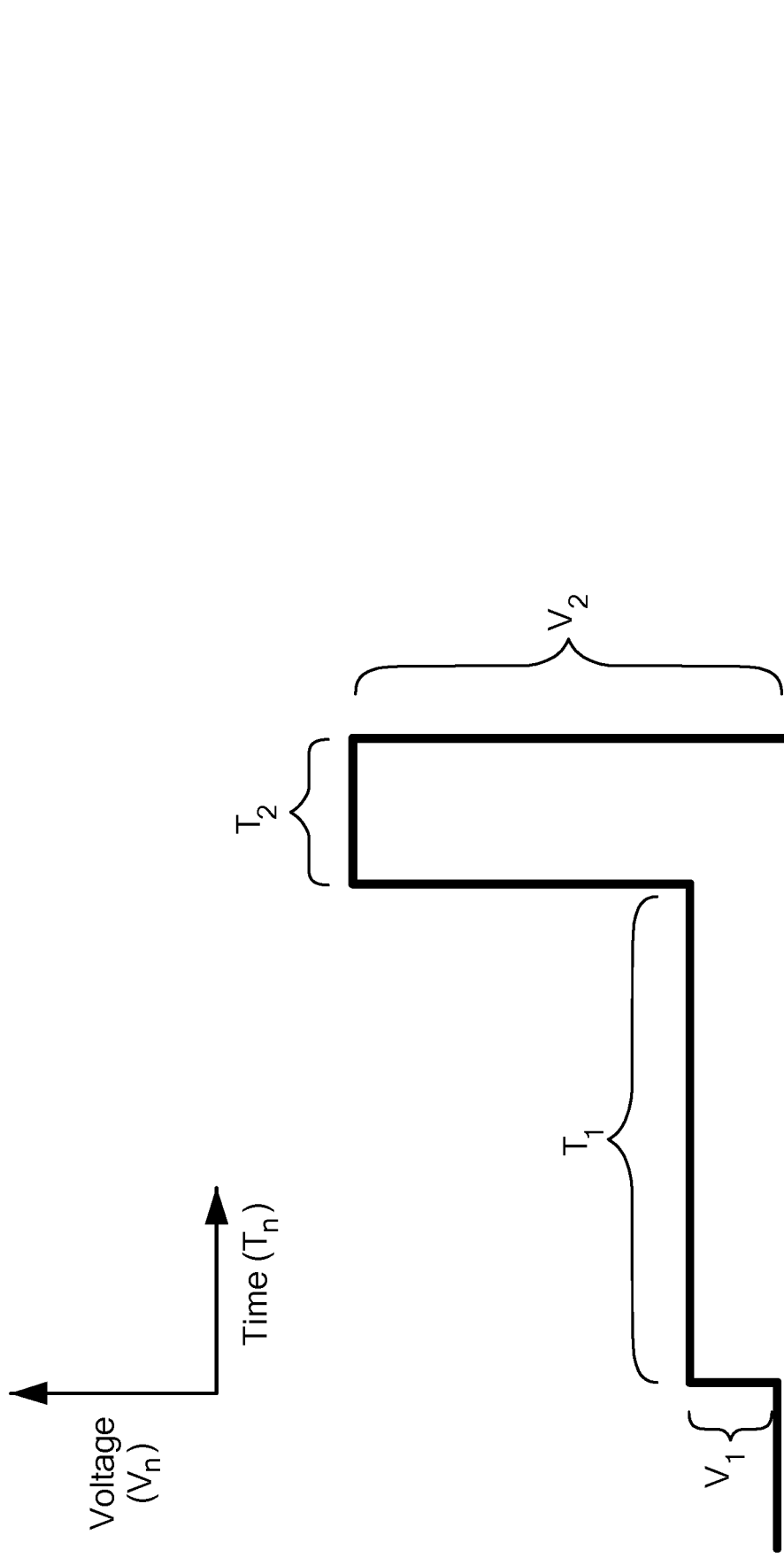
FIG. 6 is a diagram of another electroporation pulse waveform of the present application.

Referring now to FIG. 4, in another configuration of a pulsed electroporation waveform, the stacked potential waveform is substantially the same as the waveform shown in FIG. 3 except that the polarity of V2 in FIG. 4 is reversed from the polarity of V2 in FIG. 3. A second therapeutic pulse may be delivered following and inter-pulse width T6 that is opposite in polarity from the first therapeutic pulse. In another configuration of a pulsed electroporation waveform shown in FIG. 5, the stacked potential waveform, V2 may be the first pulse in the waveform followed by V3 for a time duration of T3, followed by a voltage drop to baseline. In such a configuration, V2 may function to push the ions through the cell member following the large pulse which is primarily responsible for the permeabilization. In FIG. 6, V3 may be the first pulse applied for a time duration of T3 following by V2 for a time duration of T2. Although not shown in the drawings, it is contemplated that multiple low amplitude pulses may be stacked in increasing or decreasing amplitude either before or after the larger amplitude pulse V2. For example, the voltage amplitudes may gradually increase from pulse to pulse leading up to V2 and may gradually decrease in amplitude following V2. It is further contemplated that the pulses may have alternating polarities or may include multiple pulses of V2 at the same polarity following by multiple pulses of V2 at the opposite polarity. Moreover, the absolute and/or relative voltages of each therapeutic pulse or pulses may be modified in single pulses or single applications of trains. The initiation of such modification may be automated, require human interaction, or gated on some criteria such as (for example) a combination of required waiting and timing of an associated ECG.

It will be appreciated by persons skilled in the art that the present embodiments are not limited to what has been particularly shown and described herein above. In addition, unless mention was made above to the contrary, it should be noted that all of the accompanying drawings are not to scale. A variety of modifications and variations are possible in light of the above teachings without departing from the scope of the following claims.

What is claimed is:

1. A method of delivering pulsed electrical energy to a target tissue region, comprising:
    delivering a first therapeutic pulse waveform, the delivering of the first therapeutic pulse waveform including:
       delivering a first portion of the first therapeutic pulse waveform for a first time period, the first portion of the first therapeutic pulse waveform having a first voltage amplitude and a first polarity;
       delivering a second portion of the first therapeutic pulse waveform immediately after the first portion of the first therapeutic pulse waveform for a second time period such that energy is continually delivered to the target tissue between the first and second portions of the first therapeutic pulse waveform, the second portion of the first therapeutic pulse waveform having a second voltage amplitude configured to electroporate the target tissue region, the second portion of the first therapeutic pulse waveform having a second polarity opposite the first polarity, the second time period being less than the first time period and the second voltage amplitude being greater than the first voltage amplitude; and
       delivering a third portion of the first therapeutic pulse waveform immediately after the second portion of the first therapeutic pulse waveform for a third time period such that energy is continually delivered to the target tissue between the second and third portions of the first therapeutic pulse waveform, the third time period being greater than the second time period, the third portion of the first therapeutic pulse waveform having a third voltage amplitude and the first polarity, the third voltage amplitude being less than the second voltage amplitude; and
    delivering a second therapeutic pulse waveform, the delivering of the second therapeutic pulse waveform including:
       delivering a first portion of the second therapeutic pulse waveform for a fourth time period, the first portion of the second therapeutic pulse waveform having a fourth voltage amplitude and the second polarity;
       delivering a second portion of the second therapeutic pulse waveform immediately after the first portion of the second therapeutic pulse waveform for a fifth time period such that energy is continually delivered to the target tissue between the first and second portions of the second therapeutic pulse waveform, the second portion of the second therapeutic pulse waveform having a fifth voltage amplitude configured to electroporate the target tissue region, the second portion of the second therapeutic pulse waveform having the first polarity, the fifth time period being less than the fourth time period and the fifth amplitude being greater than the fourth voltage amplitude; and
       delivering a third portion of the second therapeutic pulse waveform immediately after the second portion of the second therapeutic pulse waveform for a sixth time period such that energy is continually delivered to the target tissue between the second and third portions of the second therapeutic pulse waveform, the sixth time period beating greater than the fifth time period, the third portion of the second therapeutic pulse waveform having a sixth voltage amplitude and the second polarity, the sixth voltage amplitude being less than the fifth voltage amplitude.

2. The method of claim 1, wherein:
    delivering the first therapeutic pulse waveform includes:
       not delivering energy during a seventh time period, the seventh time period following the delivery of the third portion of the first therapeutic pulse waveform.

3. The method of claim 1, further including delivering at least one pulse train, each of the at least one pulse train having between 1-500 therapeutic pulse waveforms.

4. The method of claim 1, wherein the first voltage amplitude is in the range of 1V to 400V.

5. The method of claim 1, wherein the first time period is in the range between 4 μs and 500 ms.

6. The method of claim 1, wherein the third time period is the same as the first time period and the sixth time period is the same as the fourth time period.

7. The method of claim 1, wherein the third time period is less than the first time period.

8. The method of claim 1, wherein delivering the first therapeutic pulse includes:
    not delivering energy during the fourth time period, the fourth time period following the delivery of the third portion; and
    delivering a fourth portion for the fifth time period, the fourth portion having a fourth amplitude having a polarity opposite the polarity of the first portion.

9. The method of claim 8, wherein delivering the first therapeutic pulse includes:
    delivering a fifth portion after the fifth time period for a sixth time period, the fifth portion having fifth voltage amplitude having a polarity opposite of the second portion.

* * * * *